United States Patent [19]
Hassler et al.

[11] Patent Number: 5,470,345
[45] Date of Patent: Nov. 28, 1995

[54] IMPLANTABLE MEDICAL DEVICE WITH MULTI-LAYERED CERAMIC ENCLOSURE

[75] Inventors: Beth A. Hassler, White Bear Lake; Adrianus P. Donders, Andover, both of Minn.

[73] Assignee: Medtronic, Inc., Minneapolis, Minn.

[21] Appl. No.: 260,866

[22] Filed: Jun. 16, 1994

[51] Int. Cl.⁶ .................................................. A61N 1/375
[52] U.S. Cl. ............................ 607/36; 607/2; 361/736
[58] Field of Search .............................. 607/36, 2, 116, 607/37, 57, 60, 61, 54, 39, 40, 42–46, 32; 361/736, 752, 820; 174/52.1, 52.4, 52.2, 262

[56] References Cited

U.S. PATENT DOCUMENTS

| | | | |
|---|---|---|---|
| 4,231,098 | 10/1980 | Tanimoto | 361/736 |
| 4,288,841 | 9/1981 | Gogal | 361/414 |
| 4,604,677 | 8/1986 | Suzuki et al. | 361/736 |
| 4,614,194 | 9/1986 | Jones et al. | 607/2 |
| 4,616,655 | 10/1986 | Weinberg et al. | 607/2 |

*Primary Examiner*—William E. Kamm
*Assistant Examiner*—Kennedy J. Schaetzle
*Attorney, Agent, or Firm*—Michael B. Atlass; Harold R. Patton

[57] ABSTRACT

An implantable medical device has a novel ceramic enclosure with joinable multi-layered clamshells. In the preferred embodiment one half of the enclosure carries the hybrid circuitry and feedthroughs of, for example, a pacemaker, while, the other half carries a battery. The advantages over the prior art include higher transparency to radio frequency waves (for telemetry purposes), and reduced costs and construction time.

21 Claims, 5 Drawing Sheets

IMPLANTABLE MEDICAL DEVICE WITH MULTI-LAYERED CERAMIC ENCLOSURE

FIELD OF THE INVENTION

The present invention relates to the packaging of implantable medical devices such as artificial cardiac pacemakers and the like.

BACKGROUND OF THE INVENTION

Generally speaking, a cardiac pacemaker or implantable pulse generator (IPG) is an electrical device used to supplant some or all of an abnormal heart's natural pacing function, by delivering appropriately timed electrical stimulation signals designed to cause the myocardium of the heart to contract or "beat".

Using telemetry, modern pacemakers are often programmable with regard to data and functionality prior to, and even after implant. Typical pacemakers are enclosed by metal casings such as titanium, which has good body compatibility. However, metal enclosures often cause interference during telemetry.

To create pacemakers and other implantable medical devices with enclosures which are transparent to radio frequency (RF) waves during telemetry, the enclosure can be constructed of ceramic material, for example. Such is the approach of U.S. Pat. No. 4,785,827 issued to Fischer, and U.S. Pat. No. 4,991,582 issued to Byers et al. Both references are hereby expressly incorporated by reference.

Implantable medical devices of the above-mentioned type have a hybrid circuit with feedthroughs attached thereto and leading through a glass-to-metal feedthrough substrate to the connector block for electrical coupling to a lead (for stimulating, sensing, or both functions). As a result of the construction of prior art substrates, fewer feedthroughs can be handled than is desirable, and costs of producing such substrates is expensive.

SUMMARY OF THE INVENTION

In view of the foregoing, it is a first object of the present invention to provide an implantable medical device which is nearly transparent to radio frequency waves for telemetering purposes, especially in the 400 kilohertz to 40 megahertz frequency range.

It is a second object of the present invention to provide an implantable medical device wherein its feedthrough substrate provides for a higher density of feedthroughs.

It is a third object of the present invention to provide an implantable medical device wherein its feedthrough substrate is less expensive than prior art feedthrough substrates.

It is a fourth object of the present invention to provide an implantable medical device satisfying the above objects wherein its enclosure is ceramic.

It is a fifth object of the present invention to provide an implantable medical device wherein the enclosure walls are electrically conducting.

In order to satisfy the above objects and others, the present invention provides a packaging arrangement for the outer packaging of an implantable medical device at least including:

a first multi-layered enclosure shell; and
a second multi-layered enclosure shell;
wherein the enclosure shells are joinable to sealably enclose components of the implantable medical device, and layers of the enclosure shells are adapted to conduct signals between implantable medical device components mounted on the shells.

The details of the present invention will be revealed in the following description, with reference to the drawing.

BRIEF DESCRIPTION OF THE DRAWINGS

The various figures of the drawing are briefly described as follows.

DETAILED DESCRIPTION OF THE INVENTION

Figure 1:
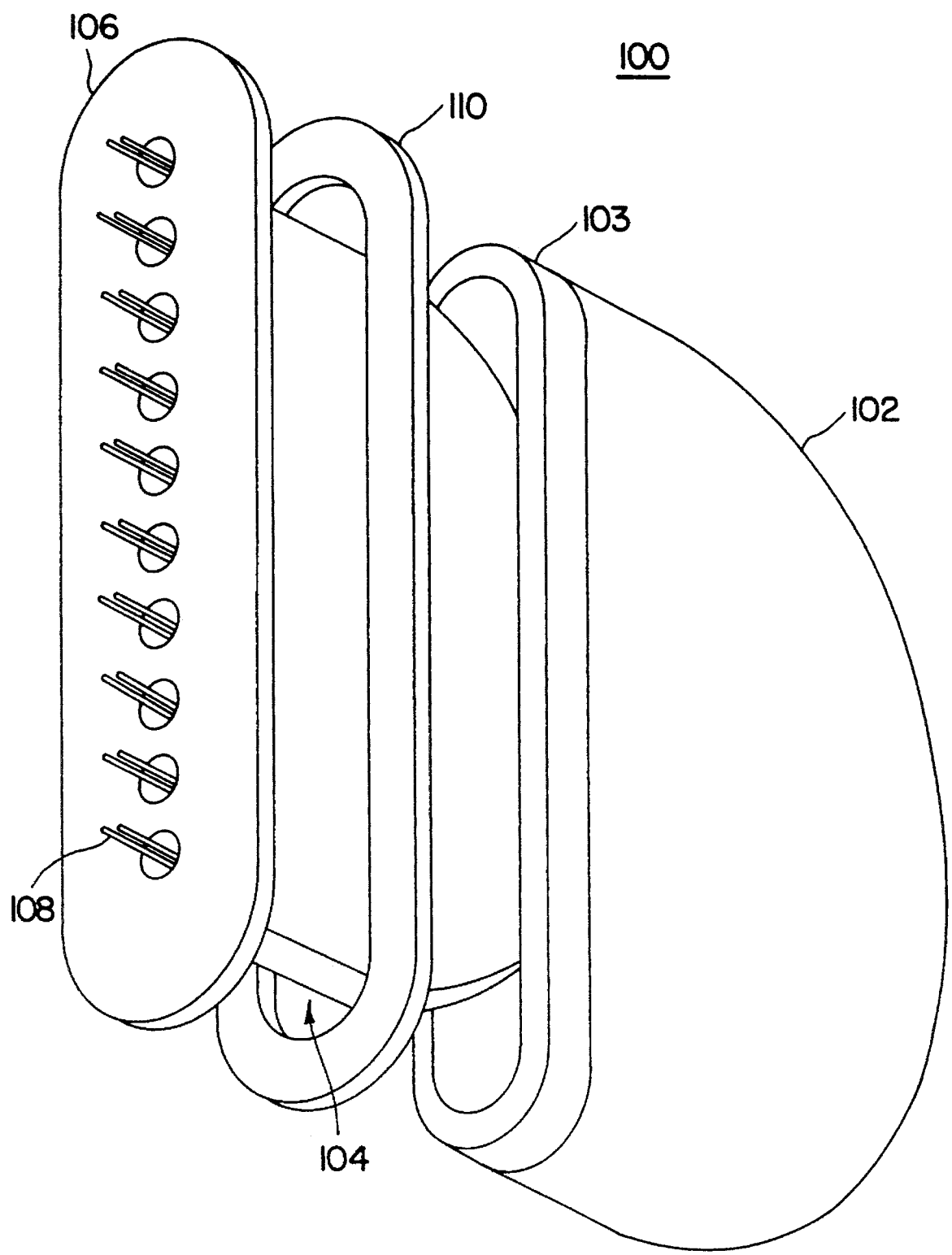
FIG. 1 is an exploded isometric view of a prior art pacemaker with a ceramic enclosure.

FIG. 1 shows a prior art packaging arrangement/scheme 100 for a pacemaker. The arrangement 100 has a ceramic enclosure 102 with a metalized portion 103. A hybrid circuit 104 is attached to a feedthrough substrate 106 which is a glass-to-metal feedthrough assembly. Feedthroughs 108 (metal) electrically connect to components of the hybrid circuit 104 at one end, and are adapted to electrically connect a connector block (not shown) at the other (exposed) end. A weld ring 110 is welded on one side to the enclosure 102 (at the metalized portion 103), and on its other side to the glass-to-metal feedthrough 106. The entire packaging provides an implantable medical device which is hermetically sealed.

Figure 2:
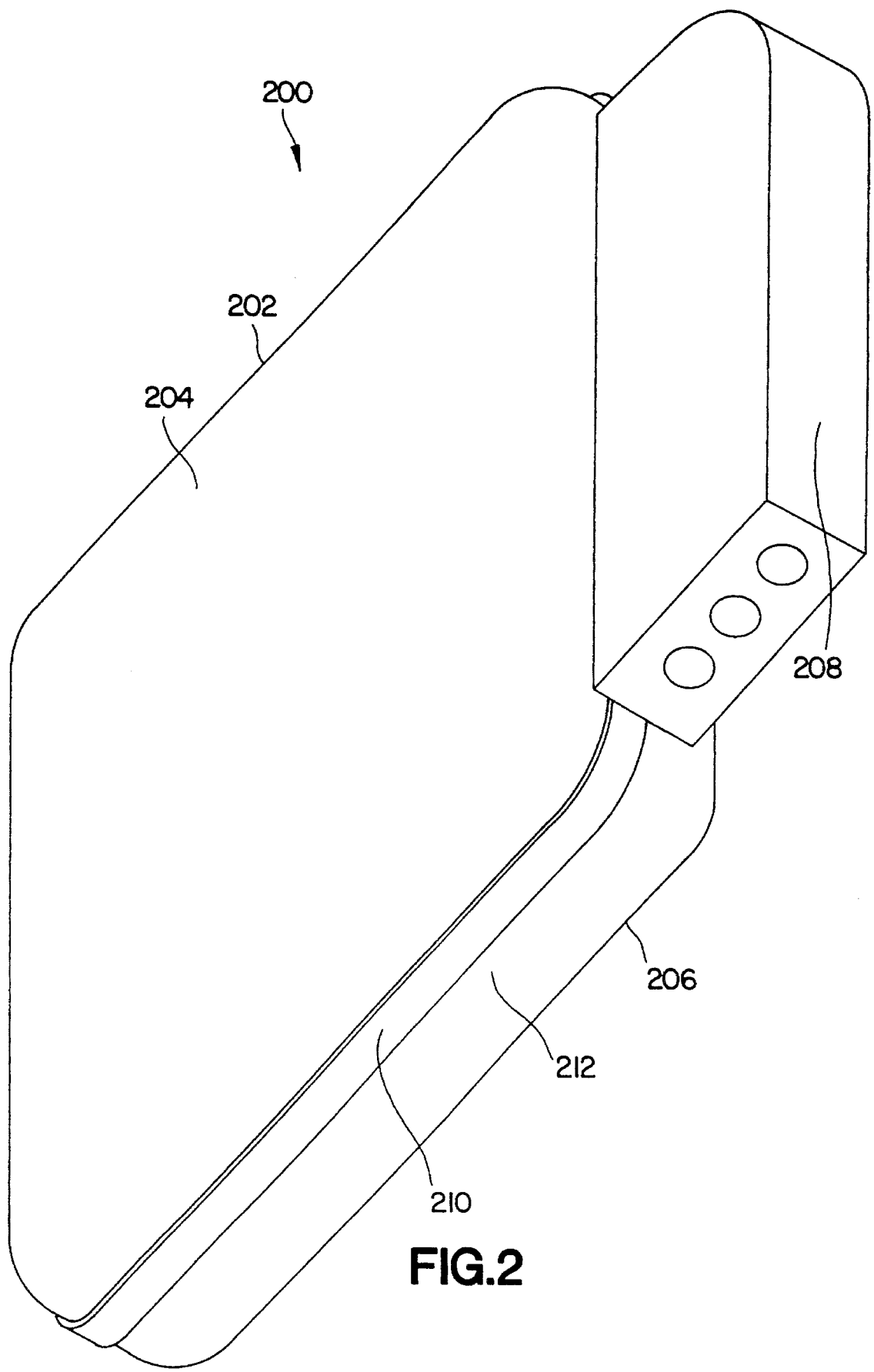
FIG. 2 is a isometric view of a pacemaker employing the present-inventive ceramic enclosure.

FIG. 2 shows an implantable medical device 200 employing the ceramic enclosure 202 of the present invention. In this case a pacemaker has two ceramic enclosure halves (or shells) 204 and 206 which are joined by weld rings 210 and 212 to form a hermetic seal. Each half 204 and 206 has a thin metalized layer for brazing the weld rings 210 and 212 thereto, respectively.

A connector block 208 is attached to the enclosure 202. In the preferred embodiment, the enclosure half 204 carries a battery (not shown) mounted to its inside wall, while the enclosure half 206 carries both a hybrid electronic circuit and feedthroughs (see FIG. 4) for connecting to the connector block 208. The feedthroughs provide an electrical connection between the hybrid circuitry and stimulation and sensing leads when attached to the connector block 208.

Figure 3:
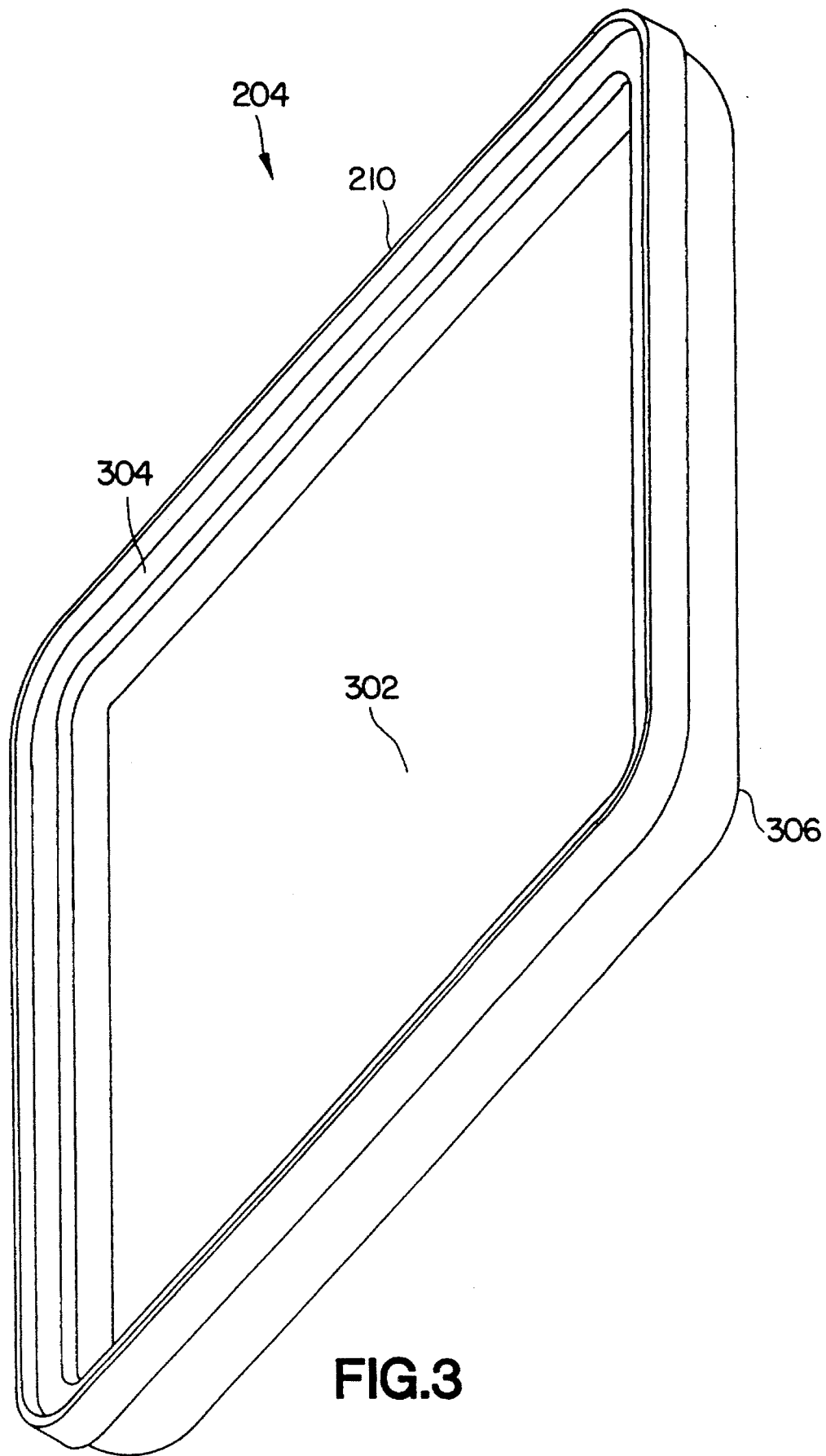
FIG. 3 is an isometric view of the battery-carrying half of the ceramic enclosure of the present invention.

The enclosure half 204 is shown in greater detail in FIG. 3. The walls of the ceramic enclosure halves 204 and 206 are constructed of multiple ceramic layers (302 in FIG. 3), variously containing electrical conduction areas, vias for inter-layer communication, and electromagnetic interference (EMI) shielding areas. The layers may be constructed of biocompatible 99.5 percent aluminum oxide, for example, which has been shown to have good tissue compatibility.

The ceramic enclosure shells 204 and 206 can be constructed using techniques known in the art, such as is disclosed by Beth A. Hassler in "Fast Turnaround Multilayer Coilred Ceramic Motherboard Fabrication," *Proceedings of ASM's 2nd Electronic Packaging: Materials and Processes*

*Conference* (October 1985): 117–121. The abovementioned article is hereby incorporated by reference.

Thin ceramic layers are joined, and then form-molded at the corners (e.g., 306). A metalized portion 304 is formed by sputtering (as is known in the art) a thin film of niobium on the ceramic surface. This provides good braze-bonding characteristics for attaching the ceramic wall to the weld ring 210. The weld ring 212 is attached to the enclosure half 206 in the same manner.

Figure 4:
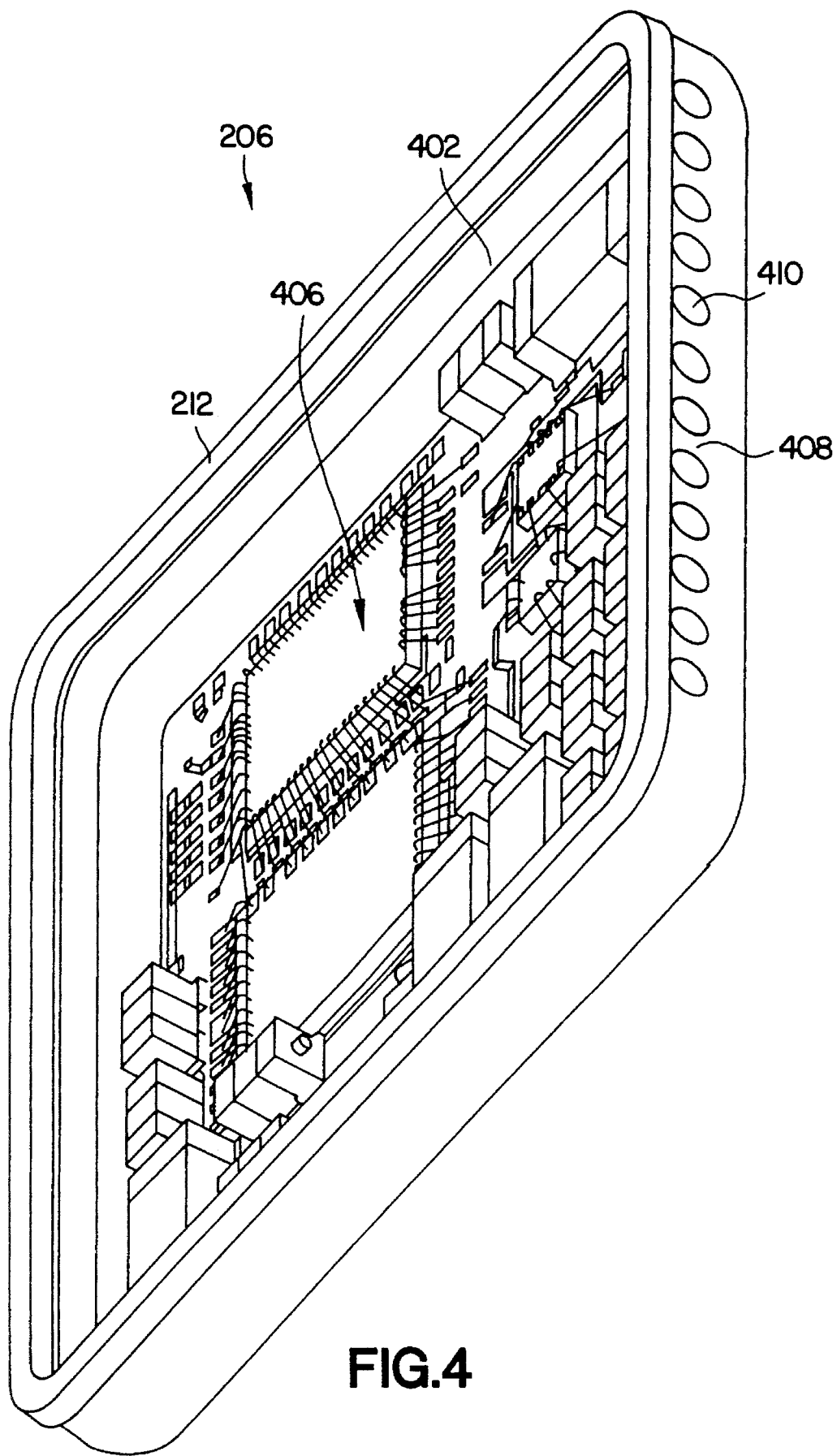
FIG. 4 is an isometric view of the hybrid circuit- and feedthrough-carrying half of the ceramic enclosure of the present invention.

The enclosure half 206 is detailed in FIG. 4. The multi-layered nature of the wall 402 of the ceramic enclosure half 206 allows the hybrid circuitry 406 of the pacemaker to be mounted directly on the ceramic enclosure, thereby saving time, money and parts compared with prior art ceramic enclosures (which do not electrically connect the enclosed components).

In addition to the hybrid circuitry, the enclosure half 206 also has a feedthrough area 408. The several layers of the ceramic material have metal-plated input/output vias used to electrically connect the various layers. The plating metals may be gold and nickel, for example. As a result of the multi-layer and via configuration, a higher density of feedthroughs 410 are possible over the glass-to-metal substrate (element 106 in FIG. 1) approaches in the prior art. The feedthroughs 410 electrically connect the circuitry carried by the enclosure to the connector block 208.

The weld ring 210 is chosen to have thermal expansion characteristics sufficiently similar to the ceramic material used to maintain good bonding over a broad temperature range.

Figure 5:
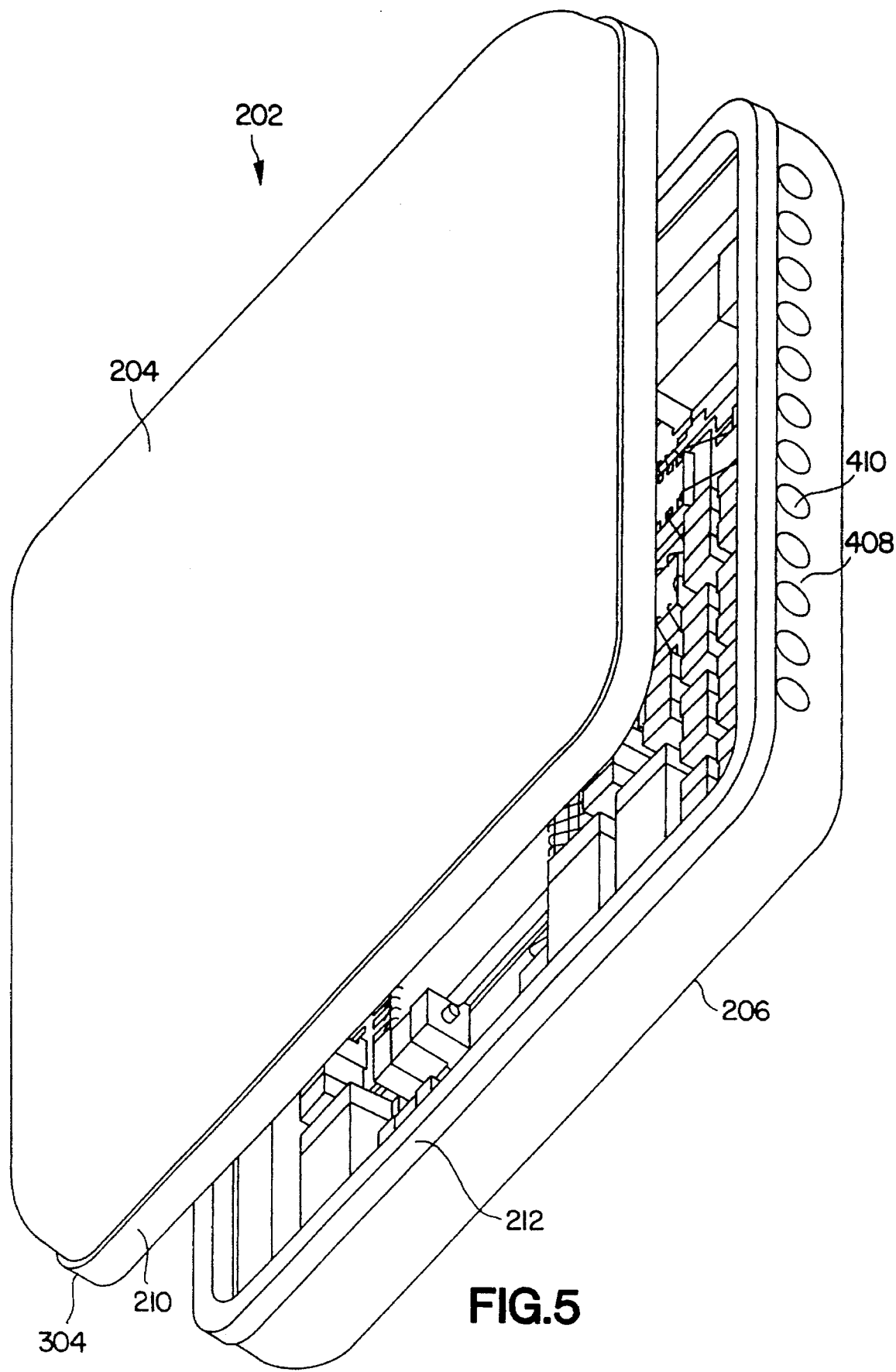
FIG. 5 is an exploded isometric view of the pacemaker in FIG. 2, without a connector block.

FIG. 5 shows an exploded isometric view of the ceramic enclosure 202 for illustrative purposes.

Variations and modifications to the present invention are possible given the above disclosure. However, such variations and modifications are intended to be within the scope of the invention claimed by this letters patent. For example, the packaging arrangement described supra. is optimal for bipolar pacing. The ceramic enclosure shells 204 and 206 may be coated with a thin metal layer (using sputtering techniques, for example) to enable unipolar pacing.

Also, bonding of the enclosure shells of the present invention need not be limited to the use of brazing and welding techniques.

We claim:

1. A packaging arrangement for the outer packaging of an implantable medical device comprising:

at least a first multi-layered enclosure shell; and at least a second multi-layered enclosure shell;

wherein said enclosure shells are joinable to sealably enclose components of said implantable medical device, and layers of said enclosure shells are adapted to conduct signals between implantable medical device components mounted on said shells.

2. The packaging arrangement of claim 1 wherein the layers of said enclosure shells are ceramic.

3. The packaging arrangement of claim 1 wherein at least one of said enclosure shells comprises a multi-layered feedthrough having multiple feedthroughs for electrically coupling circuitry mounted on said shell to the outside of said shell.

4. The packaging arrangement of claim 2 wherein at least one of said enclosure shells comprises a multi-layered feedthrough having multiple feedthroughs for electrically coupling circuitry mounted on said shell to the outside of said shell.

5. The packaging arrangement of claim 1 wherein said first enclosure shell is adapted to carry a hybrid circuit of a pacemaker, and said second enclosure shell is adapted to carry a battery circuit of said pacemaker.

6. The packaging arrangement of claim 2 wherein said first enclosure shell is adapted to carry a hybrid circuit of a pacemaker, and said second enclosure shell is adapted to carry a battery circuit of said pacemaker.

7. The packaging arrangement of claim 3 wherein said first enclosure shell is adapted to carry a hybrid circuit of a pacemaker, and said second enclosure shell is adapted to carry a battery circuit of said pacemaker.

8. The packaging arrangement of claim 4 wherein said first enclosure shell is adapted to carry a hybrid circuit of a pacemaker, and said second enclosure shell is adapted to carry a battery circuit of said pacemaker.

9. The packaging arrangement of claim 1 further comprising a connector block for coupling to said enclosure shells.

10. The packaging arrangement of claim 2 further comprising a connector block for coupling to said enclosure shells.

11. The packaging arrangement of claim 3 further comprising a connector block for coupling to said enclosure shells.

12. The packaging arrangement of claim 4 further comprising a connector block for coupling to said enclosure shells.

13. The packaging arrangement of claim 5 further comprising a connector block for coupling to said enclosure shells.

14. The packaging arrangement of claim 6 further comprising a connector block for coupling to said enclosure shells.

15. The packaging arrangement of claim 7 further comprising a connector block for coupling to said enclosure shells.

16. The packaging arrangement of claim 8 further comprising a connector block for coupling to said enclosure shells.

17. The packaging arrangement of claim 2 wherein said enclosure shells further comprise an outer metallic layer.

18. The packaging arrangement of claim 4 wherein said enclosure shells further comprise an outer metallic layer.

19. The packaging arrangement of claim 6 wherein said enclosure shells further comprise an outer metallic layer.

20. The packaging arrangement of claim 8 wherein said enclosure shells further comprise an outer metallic layer.

21. The packaging arrangement of claim 10 wherein said enclosure shells further comprise an outer metallic layer.

\* \* \* \* \*